United States Patent [19]

Mausner

[11] Patent Number: 5,204,105
[45] Date of Patent: Apr. 20, 1993

[54] COSMETIC COMPOSITION

[75] Inventor: Jack Mausner, New York, N.Y.

[73] Assignee: Chanel, Inc., New York, N.Y.

[21] Appl. No.: 508,070

[22] Filed: Apr. 10, 1990

[51] Int. Cl.$^5$ .............................................. A61K 7/032
[52] U.S. Cl. ..................................... 424/401; 424/63;
424/70; 424/195.1; 424/450; 514/21; 514/63;
514/844; 514/847
[58] Field of Search ................... 424/63, 70, 450, 401,
424/195.1; 514/844, 21, 63, 847

[56] References Cited

U.S. PATENT DOCUMENTS

| | | | |
|---|---|---|---|
| 3,697,643 | 10/1972 | Shepherd et al. | 424/70 |
| 3,864,275 | 2/1975 | Kan et al. | 264/4.7 |
| 3,911,105 | 10/1975 | Papantoniou et al. | 424/64 |
| 3,966,398 | 6/1976 | Vanlerberghe | 424/70 |
| 4,125,549 | 11/1978 | Coopersmith et al. | 554/170 |
| 4,247,411 | 1/1981 | Vanlerberghe et al. | 264/4.6 |
| 4,369,037 | 1/1983 | Matsunaga et al. | 8/127.51 |
| 4,400,295 | 8/1983 | Ootso | 514/784 |
| 4,423,031 | 12/1983 | Murui et al. | 424/63 |
| 4,460,371 | 7/1984 | Abber | 424/449 |
| 4,481,186 | 11/1984 | Deckner | 424/59 |
| 4,549,990 | 10/1985 | Sequin et al. | 552/544 X |
| 4,608,392 | 8/1986 | Jacquet et al. | 514/772 |
| 4,752,496 | 6/1988 | Fellows et al. | 427/27 |
| 4,758,599 | 7/1988 | Minetti | 514/355 |
| 4,883,659 | 11/1989 | Goodman | 424/70 |
| 4,927,952 | 5/1990 | Gueyne et al. | 556/419 |
| 5,037,803 | 8/1991 | Gueyne et al. | 514/2 |

*Primary Examiner*—Thurman K. Page
*Assistant Examiner*—Robert H. Harrison
*Attorney, Agent, or Firm*—Denton L. Anderson

[57] ABSTRACT

An emulsified composition for treatment of the skin under the eye comprises means for reducing puffiness of the skin under the eyes and for reducing sensations of irritation and inflammation of the skin under the eyes. There is means for enhancing firmness and elasticity of the skin under the eyes and for reducing dark circles, and means for retarding the effects of free radical activity under the eyes. A preservative, thickener, antioxidant, emulsifier and solvent can be part of the composition.

3 Claims, No Drawings

COSMETIC COMPOSITION

BACKGROUND

Enhancing the appearance of the skin is an age old desire. This invention is directed to a cosmetic composition for the skin, specifically the skin beneath the eye.

"Bags" beneath the eyes is a widespread, cosmetic problem and occurs when the skin of the lower eye lid hangs loose, pouchlike or puffy. This condition is caused by aging, various diseases, and environmental factors that irritate the eyes and the surrounding skin. An accompanying feature of this condition is frequently dark circles under the eyes.

The skin surrounding the eye is relatively thin-layered and contains less fat than most other areas of skin. For this reason, the effects of aging, stress, diseases, and environmental pollution are first seen as puffiness, bags or rings beneath the eyes. The firmness and elasticity of the skin of the lower eyelid is lost. Environmental factors causing puffiness of eyes include particulate air pollution from industrial and automotive exhaust.

People often resort to cosmetic surgery to remove bags beneath the eyes and restore the smoothness of the lower eyelids. The problems with cosmetic surgery include its great expense and risks of anesthesia and infection that accompany every surgical procedure.

Cosmetic products for application to the skin beneath the eye contain ingredients, such as plant extracts, aimed solely at making the lower eyelids feel comfortable and soothed. This merely amounts to relieving surface irritations, and does not address the cosmetic problems of the skin in order to restore elasticity and firmness to puffy skin beneath the eye.

Accordingly, there is a need for a cosmetic product that is effective in (a) retarding formation of bags beneath the eyes, (b) partially or fully restoring a smooth skin contour to puffy skin beneath the eye, and (c) minimize dark circles under the eyes.

SUMMARY

The present invention provides a cosmetic composition particularly directed to satisfying this need. The cosmetic product can reduce puffy skin beneath the eye, making the contour of the skin smoother, and it can reduce dark circles under the eye.

For the skin under the eye, the emulsified cosmetic composition of the present invention comprises agents which reduce puffiness, improve the firmness, minimize dark circles, relieve irritation of the skin beneath the eye caused by environmental pollution, and prevent weakening effects of natural free radical activity in the skin on the skin's firmness, as well as reduce dark circles under the eyes.

The product that accomplishes these results is an emulsified cosmetic composition comprising a water and an oil phase. Dispersed in the water and oil phases is an agent for reducing puffiness of the skin under the eyes and for reducing sensations of irritation and inflammation of the skin under the eyes. There is also an agent for enhancing firmness and elasticity of the skin under the eyes and an agent for retarding the effects of free radical activity on the firmness of the skin under the eyes.

The agent for reducing puffiness of the skin under the eyes and for reducing sensations of irritation and inflammation of the skin under the eyes is selected from the group consisting of plant extracts and yeast extracts and combinations thereof. The plant extracts can comprise butcher broom, hydrocotyl, horse chestnut, calendula, hamamelis, horsetail, euphrasia, peach, lady's mantle, ivy, chamomile matricaria, and comfrey.

The agent for enhancing firmness and elasticity of the skin under the eyes and for minimizing dark circles under the eyes can be selected from the group consisting of silicon derivatives. A preferred silicon derivative is a complex of methylsilanol elastinate and methylsilanol aspartate hydroxyprolinate.

The agent for retarding the effects of free radical activity on the firmness of the skin under the eyes can be selected from the group consisting of derivatives of vitamins C or E, selenium metal compounds, or beta carotene derivatives.

A satisfactory composition results from using derivatives of vitamin E. A preferable composition provides vitamin E in the form of tocopherol, wheat germ glycerides, and a complex comprised of vitamin E and lipids which are found in the surface layers of human skin. These lipids are commercially obtained in soluble form and known commercially as "soluceramides." The lipids, solubilized in the solvent octyldodecanol, can be lecithin, phosphatidyl ethanolamine, and phosphatidyl choline.

The cosmetic composition further comprises a preservative preventing microbial growth in the composition. A thickener increases the viscosity of the composition. An antioxidant prevents rancidity and discoloration of the composition. An emulsifier combines the water phase and oil phase as well as giving the composition a suitable texture when applied to the skin.

The invention is further described in the following detailed description.

DESCRIPTION

An emulsified cosmetic composition comprises an aqueous base. Emulsified and dispersed in the water is an agent for reducing puffiness of the skin and for reducing sensations of irritation and inflammation of the skin. The composition contains an agent for enhancing firmness and elasticity of the skin and an agent for retarding the effects of free radical activity on the firmness of the skin.

The cosmetic composition is an emulsified base and is particularly suitable for treatment of the skin under the eyes.

Cosmetic compositions containing plant extracts and silicon derivatives were formulated for relieving topical irritation of skin and for promoting skin firmness. Moreover, compositions were prepared for retarding the effects of free radical activity on the skin. These compositions included silicon derivatives, plant extracts, vitamin E and skin lipids, and yeast extract. A particularly unique product that was surprisingly effective in reducing puffiness of the skin beneath the eye resulted with the addition of yeast extract to the combination of plant extracts, silicone derivatives and complex of vitamin E and skin lipids. Cosmetic compositions for treatment of the skin are to be considered separately as a first part as being (1) for reducing puffiness of the skin and for reducing sensations of irritation and inflammation of the skin, (2) for enhancing firmness and elasticity of the skin, and (3) for minimizing dark circles under the eyes. The unique effectiveness of this first part is due to the particular combination resulting from the addition of yeast extract. A second part is an agent for retarding the effects of free radical activity on the firmness of the skin, which in combination with the first part provides an exceptionally effective product for reducing puffiness beneath the eyes. In addition to being considered as a first part, the cosmetic composition can be considered collectively both of these parts.

The cosmetic composition was prepared according to the preferred concentrations listed in Table 1. Table 1 also shows the range of concentrations of the ingredients which are possible. These ingredients are dispersed in an emulsified composition by the method of preparation discussed below. "Dispersal" refers to any process by which the ingredients are uniformly distributed in the emulsified base, and includes dissolving, emulsifying, and forming a colloidal suspension. Dispersal involves sufficient mixing until visual inspection of samples reveals an absence of powder or lumps in the composition. Table 1 provides details about the ingredients and presents a preferred concentration of plant extracts (11-165 of the composition). Each of the various ingredients will now be discussed.

Ingredients for reducing puffiness and sensations of irritation

The agents for reducing puffiness and sensations of irritation in the skin under the eye are selected from the group consisting of plant extracts and yeast extract. Commercial sources for the plant extracts and yeast extract make up the emulsified composition. These ingredients are supplied in various combinations. The commercial source for some of the plant extracts and yeast extract is Vegetal Amino Complex LS 2376 ("V.A.C."), available from Laboratoires Serobiologiques, Inc., Somerville, N.J. The following commercial sources for plant extracts are: (a) Hamamelis extract available from E. E. Dickenson Co., Essex, Conn.; (b) Horsetail extract available from Bourjois, S. A., Paris, France; (c) Spiraea extract available from Gattefosse' Corporation, Hawthorne, New Jersey; (d) Euphrasia extract available from Active Organics, Van Nuys, CA; (e) Peach extract available from Active Organics, Van Nuys, Calif.; (f) Lady's Mantle extract available from Active Organics, Van Nuys, Calif.; (g) Ivy extract available from Gattefosse' Corporation, Hawthorne, N.J.; (h) Chamomile Matricaria extract available from Gattefosse' Corporation, Hawthorne, N.J.; and (i) Comfrey extract available from Laboratories Serobiologiques, Inc., Somerville, N.J.

The active ingredients of V.A.C. are plant extracts and a yeast extract. The plant extracts are butcher broom, hydrocotyl, horse chestnut, and calendula. The respective weight ratios of these ingredients in V.A.C. are presented in Table 2. V.A.C. further contains propylene glycol functioning as a solvent and D-panthenol serving as an emollient.

Ingredients for enhancing firmness and elasticity

The agents for enhancing firmness and elasticity of the skin and for minimizing under eye circles can be selected from the group consisting of silicon derivatives. Preferred is a silicon derivative that comprises a complex of methylsilanol elastinate and methylsilanol aspartate hydroxyprolinate. The concentration of this complex in the emulsified cosmetic composition can range from 3.4% to 4.6%. Four per cent is the preferred concentration. The preferred respective weight ratios of methylsilanol elastinate and methylsilanol asparatate hydroxyprolinate in the complex are 25% and 75%. A commercial source of methylsilanol elastinate and methylsilanol aspartate hydroxyprolinate is Exsymol S.A.M. (Monte Carol, Monaco). Methylsilanol elastinate is sold under the trade name of "Proteosilane-C" and methylsilanol aspartate hydroxyprolinate is sold under the trade name of "Hydroxyprolisilane-C".

Ingredients for reducing effects of free-radicals

The anti-free radical ingredients of the emulsified cosmetic composition can be selected form the group consisting of derivatives of vitamins C or E, selenium metal compounds, or beta carotene derivatives. Preferably, the emulsified cosmetic composition is made with vitamin E derivatives consisting of tocopherol, wheat germ glycerides, and a complex of vitamin E and "soluceramides" in the respective weight ratios presented in Table 1. "Soluceramides" is a trade name of a product available from Laboratories Serobilogiques, Inc., Somerville, N.J. The product contains lipids found in the surface layers of human skin. These lipids are lecithin, phosphatidyl ethanolamine, and phosphatidyl chlorine dissolved in octyldodecanol and combined with tocopheryl acetate, as shown in Table 1.

Preservatives

Preservatives are employed in the emulsified cosmetic composition because it is manufactured under clean but non-sterile conditions. Preservatives are used to prevent the growth of microbes. A sufficient quantity of one or more preservatives is added so that the emulsified cosmetic composition withstands the growth of bacteria from an experimental inoculation for at least three months.

The emulsified composition can be prepared with a commercially obtained preservative composition known as Phenonip (TM). Phenonip (TM) is a practically colorless, viscous, liquid mixture of phenoxyethanol, methylparaben, ethylparaben, propylparaben, and butylparaben available from Nipa Laboratories, Inc., Wilmington, Del. Table 1 shows the agents which comprise phenonip (TM).

TABLE 1

Composition of the Emulsified Cosmetic Composition

| Ingredient | Content of the Ingredient | Concentration of the Content in the Ingredient (%) |
|---|---|---|
| Vegetal amino complex (1-3% of the composition) | Water | 95.0 |
| | D-panthenol | 0.5 |
| | Propylene glycol | 1.5 |
| | Butcher broom extract | 1.5 |
| | Hydrocotyl extract | 0.5 |
| | Horse chestnut extract | 0.5 |
| | Calendula extract | 0.3 |
| | Yeast extract | 0.2 |
| Plant extracts (11-16% of the composition) | Hamamelis | |
| | Horsetail | |
| | Euphrasia | |
| | Peach | |
| | Lady's mantle | |
| | Ivy | |
| | Chamomile matricaria | |
| | Comfrey | |
| Silicon Derivatives (3.4-4.6% of the composition. 4% is preferred.) | Complex of: 1. methylsilanol elastinate 2. methylsilanol aspartate hydroxyprolinate | |
| Anti-Free Radical Agents | Tocopherol | 0.8-0.12 |
| | Wheat germ glycerides | 0.13-0.17 |
| | Vitamin E and soluceramides | 0.8-1.2 |

TABLE 1-continued

Composition of the Emulsified Cosmetic Composition

| Ingredient | Content of the Ingredient | Concentration of the Content in the Ingredient (%) |
|---|---|---|
| | complex comprised of lecithin, phosphatidyl ethanolamine and phosphatidyl choline dissolved in octyldodecanol and combined with tocopheryl acetate. | |
| Preservatives | Ascorbyl ester | 0.01-0.02 |
| | Phenonip TM : phenoxyethanol methylparaben ethylparaben propylparaben butylparaben | 0.6-0.9 |
| Thickener | Carbopol 1342 Resin TM : | |
| | $C_{10}$-$C_{30}$ alkyl acrylates cross-polymer | 0.6-0.8 |
| | carrageenan | 0.3-0.5 |
| | xanthan gum | 0.02-0.3 |
| Emulsifiers | Propylene glycol isoceteth-3 acetate | 3.4-4.6 |
| | Laureth-2 benzoate | 4.0-6.0 |
| | Diisostearyl dimer dilinoleate | 1.0-2.0 0.9-1.2 |
| | Unsaturated fatty acid ester | 3.4-4.6 |
| | Short-chain saturated fatty acid ester | 9.0-11.0 |
| | Glyceryl ester | 0.12-0.16 |
| | 85% triethanolamine | |
| Antioxidant | Ascorbyl ester: ascorbyl palmitate, ascorbyl myristate, or ascorbyl stearate | 0.01-0.02 |
| Solvents | Triple-distilled rose water | 10.0-14.0 |
| | 1,3-butylene glycol | 5.0-7.0 |
| | Demineralized water | 79-85 |
| Pigment | Red iron oxide | |

Thickeners

Sufficient thickeners are employed so that the cosmetic composition does not run off the lower eyelid when applied. The thickeners complement the function of the emulsifiers in holding together the water and oil phases of the composition. The emulsified composition preferably employs as thickeners acrylates, xanthan gum and carrageenan. The acrylates are obtained commercially as a product known as Carbopol 1342 Resin (TM), available from B. F. Goodrich Co., Cleveland, Ohio. Carbopol 1342 Resin (TM) contains copolymer of carboxylic acid containing monomers and acrylic esters, more specifically C10-30 alkyl acrylate cross polymer.

Antioxidants

Since the emulsified composition is applied to the skin, it is essential to a consumer that the composition's appearance and odor be pleasing. To maintain the composition's color and prevent malodorous developments, an antioxidant is included in the cosmetic composition. The antioxidant can be an ascorbyl ester selected from the group consisting of ascorbyl palmitate, ascorbyl myristate, and ascorbyl stearate. A preferred antioxidant is ascorbyl palmitate.

Emulsifiers

Emulsifiers serve two functions. They act like a solubilizing agent to combine the water soluble and non-water soluble phases together; that is, form a stable bridge between the waters and the oils of the ingredients. The emulsifiers also serve as emollients, providing a pleasant, aesthetically appropriate, tactile feeling when the emulsified composition is applied to the skin. A preferred cosmetic composition comprises emulsifiers identified in Table 1. These can be propylene glycol isoceteth-3 actetate and laureth-2 benzoate. One of the emulsifiers can be an ester of an unsaturated fatty acid selected from the group consisting of of isodecyl oleate, isononyl oleate, isoundecyl oleate, isononyl elaidate, isodecyl elaidate, isoundecyl elaidate, isononyl vaccenate, isodecyl vaccenate, and isoundecyl vaccenate. A preferred ester of an unsaturated fatty acid is isodecyl oleate.

Another emulsifier can be an ester of a short-chain saturated fatty acid selected from the group consisting of myristyl octanoate, myristyl heptanoate, myristyl nonanoate, lauryl heptanoate, lauryl octanoate, lauryl nonanoate, palmityl heptanoate, palmityl octanoate, and palmityl nonanoate. A typical ester of a short-chain saturated fatty acid for emollient use in the emulsified cosmetic composition can be myristyl octanoate.

A preferred emulsifier can be a glyceryl ester selected from the group consisting of glyceryl stearate, glyceryl palmitate, and glyceryl arachidate. A typical glyceryl ester for use in the emulsified cosmetic composition is glyceryl stearate. Other preferred emulsifiers include triethanolamine and 3-cyclohexene-1-methanol, alpha, 4-dimethyl-alpha-(4-methyl-3-pentenyl) ("bisabolol").

Solvents

Demineralized water is preferably used in the cosmetic composition as the emulsified base. Triple distilled rose water can be used as a solvent for making a mixture of plant extracts, yeast extract and silicone derivatives, as described below in the method for preparing the aqueous composition. 1,3-butylene glycol can be employed as a solvent for making a slurry of thickeners, also described below in the method.

Pigment

The cosmetic composition can include at least one pigment for coloration, preferably red iron oxide.

Method of Preparation of the Cosmetic Composition

A preferred method for manufacturing the cosmetic composition takes place over a two-day period. The various mixtures and the sequences in which they are prepared and combined are now described in some detail.

On the first day, four separate mixtures are prepared in separate containers. A first mixture is a heated composition of emulsifiers, sources of vitamin E, antioxidant, pigment and solvent. The following ingredients are combined, mixed and heated from about 60 degrees C to about 65 degrees C. until melted, then stored overnight at about 60 degrees C.: propylene glycol isoceteth-3 acetate, laureth-2 benzoate, diisostearyl dimer dilinoleate, isodecyl oleate, myristyl octanoate, bisabolol, glyceryl stearate, tocopherol, wheat germ glycerides, ascorbyl palmitate, red iron oxide and demineralized water.

A second mixture combines water with Carbopol 1342 (TM) resin, that is, C10-C30 alkyl acrylates crosspolymer. This mixture is vigorously propeller-mixed all day until dissolved. The sides, top and bottom of the container must be frequently scraped to prevent adherence of the C10-C30 alkyl acrylates cross-polymer to the container. After all-day mixing, the second mixture is allowed to sit overnight, and mixing is begun again the next morning.

A third mixture combines triple-distilled rose water with the plant extracts, vegetal amino complex, and silicone derivatives. This mixture is vigorously mixed until uniform.

A fourth mixture is formed by mixing xanthan gum and carrageenan (thickeners) with 1,3 butylene glycol, a solvent. The mixture of thickeners (the fourth mixture) is then combined with the third mixture, described above, and allowed to sit overnight.

On the second day of the procedure, the first heated mixture containing emulsifiers, sources of vitamin E, pigment, antioxidant and solvent is added to the combination of third and fourth mixtures, and mixed until sufficiently uniform. To this mixture is added the second mixture prepared the day before. After thorough mixing, this combination of first, second, third and fourth mixtures is run through a homogenizer. To this homogenized mixture is added Phenonip (TM) and the vitamin E and soluceramides complex. Finally, a mixture of triethanolamine and demineralized water is added to the homogenized mixture. This is mixed until homogeneous, forming the cosmetic composition, which can be stored cold at approximately 10 degrees C. to 15 degrees C.

Clinical Studies Showing the Effectiveness of the Cosmetic Composition in Reducing Bags Under the Eyes A clinical test of the cosmetic composition of Table 1 on 13 subjects with "bags" and dark circles under the eyes demonstrated that the composition is capable of reducing the size of "bags" found under the eyes. The research subjects were instructed to evenly apply the cosmetic composition with gentle massage to lower eyelids in the morning and at night for two weeks. Objective, quantitative measurements of the skin beneath the eye were made using an in vivo image analyzing system. The quantitative assay of the size of the "bags" before and after treatment showed an average percent decrease in the size of these "bags" of twenty eight (28%) percent. This decrease in "bag" size occured in nine of thirteen research subjects, ranging in the magnitude of improvement or decrease in "bag" size ranged from a high of 69% to a low of 3%. Four research subjects showed no change.

The subjective findings of perception of improvement of "bags" beneath the eyes supported the objective findings. Nine of the thirteen research subjects felt that the cosmetic composition decreased the size of the "bags" under their eyes. The other four subjects saw no change.

A second clinical study of the composition of Table 1 on 96 subjects with "bags" and dark circles under the eyes show that the composition reduced the size of the "bags" and reduced discoloration that is, dark rings under the eye.

The skin under the eye of the subjects was numerically graded by clinicians for puffiness/swelling and discoloration. The subjects were instructed to maintain a regimen for three weeks in which they washed the face at least twice a day and applied the composition at least twice each day, after washing.

After one, two, and three weeks of composition use, the puffiness/swelling and discoloration under each eye was numerically graded. The results indicated significant decreases in "bag" size and discoloration. More than two-thirds of the subjects showed a significant reduction in puffiness. Forty per cent of subjects showed significant decreases in discoloration.

The product has the superiority of addressing a wider variety of causes of "bags" under the eyes. The cosmetic composition has the advantage of improving the contour and firmness of the skin under the eye, while protecting against the deteriorating effects of natural free radical activity in the skin, as well as relieving surface irritation.

The emulsified cosmetic composition has multiple effects when applied to the skin. The multiple effects on the skin under the eye are: (a) reducing puffiness, (b) reducing sensations of irritation and inflammation, (c) enhancing firmness and elasticity, and (d) retarding the effects of free radical activity in the skin on firmness.

This is particularly advantageous to (a) compositions which merely apply to the skin agents that temporarily relieve surface sensations of irritation, (b) compositions which merely apply to the lower eye lids a film of rouges, tints, and other coloring agents that mask shadows caused by bags, or (c) compositions which make the skin temporarily moister.

Clinical tests reveal, surprisingly, that combining a mixture of plant extract, silicon derivative and vitamin E derivative with yeast extract markedly reduced bags under the eyes while improving skin contour and firmness. The composition appeared to produce a "lift" of the skin beneath the eyes, giving the skin a more youthful look.

Although the present invention has been described with reference to one composition, other compositions are possible. Also, although the invention has been described with reference to compositions for the skin beneath the eyes, the composition could be applied cosmetically to other areas of the skin. The spirit and scope of the invention is to be determined solely by the appended claims.

What is claimed is:

1. An emulsified cosmetic composition for treatment of skin under the eyes comprising water and emulsified and dispersed in the water:

(a) a means for reducing puffiness of the skin under the eyes and for reducing sensations of irritation and inflammation of the skin under the eyes including a mixture comprising plant extracts and yeast extract as follows:
  (1) about 1% to about 3% of a vegetal amino complex, the vegetal amino complex consisting essentially of:
    (i) about 95% water,
    (ii) about 1.5% butcher broom extract,
    (iii) about 1.5% propylene glycol,
    (iv) about 0.5% hydrocotoyl extract,
    (v) about 0.5% horse chestnut extract,
    (vi) about 0.5% D-panthenol,
    (vii) about 0.2% yeast extract, and
    (viii) about 0.3% calendula extract; and
  (2) about 11% to about 16% of a mixture of plant extracts, the mixture consisting essentially of:
    (i) hamamelis extract,
    (ii) horsetail extract,
    (iii) euphrasia extract,
    (iv) peach extract,
    (v) lady's mantle extract,
    (vi) ivy extract,
    (vii) chamomile matricaria extract, and (viii) comfrey extract;

(b) means for enhancing firmness and elasticity of the skin under the eyes and for minimizing dark circles under the eyes, the means, the silicone derivatives comprising between about 3.4% and about 4.6% of a complex of at least one of methylsilanol elastinate and methylsilanol aspartate hydroxyprolinate;

(c) means for retarding the effects of free radical activity on the firmness of he skin under the eyes selected from the group consisting of vitamin A, vitamin C, a selenium metal compound, and beta carotene;

(d) a preservative for preventing microbial growth in the composition;

(e) a thickener to increase the viscosity of the composition;

(f) an anti-oxidant; and (g) an emulsifier.

2. An emulsified cosmetic composition for treatment of skin under the eyes comprising:

water, and emulsified and dispersed in the water:

(a) means for reducing puffiness of the skin under the yes and for reducing sensations of irritation and inflammation of the skin under the eyes including a mixture consisting of plant and yeast extracts;

(b) means for enhancing firmness and elasticity of the skin under the eyes and for minimizing dark circles under the eyes comprising between about 3.4% to about 4.6% of a complex of methylsilanol elastinate and methylsilanol aspartate hydroxyprolinate;

(c) means for retarding the effects of free radical activity on the firmness of the skin under the eyes selected from the group consisting of vitamin A, vitamin C, a selenium metal compound, and beta carotene;

(d) a preservative for preventing microbial growth in the composition;

(e) a thickener to increase the viscosity of the composition;

(f) an anti-oxidant; and (g) means for emulsification.

3. An emulsified cosmetic composition for treatment of skin under the eyes comprising water and emulsified and dispersed in the water:

(a) means for reducing puffiness of the skin under the eyes and for reducing sensations of irritation and inflammation of the skin under the eyes comprising plant extracts nd yeast extract;

(b) means for enhancing firmness and elasticity of the skin under the eyes and for minimizing dark circles under the eyes comprising between about 3.4% and about 4.6% of a complex of methylsilanol elastinate and methylsilanol aspartate hydroxyprolinate;

(c) means for retarding the effects of free radical activity on the firmness of the skin under the eyes selected from the group consisting of vitamin A, vitamin C, a selenium metal compound, and beta carotene;

(d) a preservative for preventing microbial growth in the composition;

(e) a thickener to increase the viscosity of the composition;

(f) an anti-oxidant;

(g) mans for emulsification, including (i) about 3.4% to about 4.6% propylene glycol isoceteth-3 acetate;

(ii) about 4% to about 6% laureth-2 benzoate;

(iii) about 1% to about 2% diisostearyl dimer dilinoleate;

(iv) about 0.9% to about 1.2% of an ester of an unsaturated fatty acid;

(v) about 3.45 to about 4.6% of an ester of a short-chain saturated fatty acid;

(vi) about 9% to about 11% of a glyceryl ester; and (viii) about 0.12% to about 0.16% of 85% triethanolamine.

* * * * *